US United States Patent [19]  [11] 3,946,734
Dedrick et al.  [45] Mar. 30, 1976

[54] APPARATUS FOR CONTROLLING THE RELEASE OF A DRUG

[75] Inventors: Robert L. Dedrick, McLean, Va.; Robert J. Lutz, Wheaton; Daniel S. Zaharko, Rockville, both of Md.

[73] Assignee: The United States of America as represented by the Secretary of State, Washington, D.C.

[22] Filed: Feb. 19, 1975

[21] Appl. No.: 551,120

[52] U.S. Cl. ............... 128/260; 128/1 R; 128/268; 128/272
[51] Int. Cl.² A61M 5/00; A61M 7/00; A61M 31/00
[58] Field of Search ............ 128/260, 1 R, 2 F, 213, 128/272, 218 D, 268; 260/209 R; 222/386, 389; 424/19, 21, 28

[56] References Cited
UNITED STATES PATENTS

| | | |
|---|---|---|
| 3,765,414 | 10/1973 | Arlen .............................. 128/260 |
| 3,805,784 | 4/1974 | Alter .............................. 128/235 |
| 3,845,770 | 11/1974 | Theeuwes ........................ 128/260 |
| 3,865,108 | 2/1975 | Hartop ............................. 128/260 |
| 3,875,300 | 4/1975 | Homm ............................. 424/28 |

Primary Examiner—Aldrich F. Medbery

[57]  ABSTRACT

The subject invention is directed to an apparatus which selectively controls the rate with which a drug contained therein is released to surrounding tissue. Moreover, the subject invention is directed to process for controlling said release which comprises sealing the end of a suitable vessel with a non-porous material, inserting into said vessel a suitable medicament, and sealing the opposite end thereof with a porous neutral hydrogel through which naturally occuring materials can diffuse and further through which said medicament may diffuse.

7 Claims, 1 Drawing Figure

APPARATUS FOR CONTROLLING THE RELEASE OF A DRUG

BACKGROUND OF THE INVENTION

As noted our invention relates generally to a method and a means for introducing a medicament into a living organism and in particular to the use of a neutral hydrogel to selectively control the rate at which such medicaments are released within a specified region and/or organ of the body.

In the past, drugs or pharmaceutical preparations have been mixed with carrier agents, such as beeswax, peanut oil, stearates, etc., and injected intramuscularly into the body. The carrier is then slowly broken down within the body allowing a slow release of the drug. Such carriers do not give satisfactory results because they often produce undesirable effects, such as foreign body reaction and scar formation; in addition, granulomas (benign fibrous tumors) and sterile abscesses are formed at the site of the injection. In most cases the rate of release of the therapeutic agent is so rapid that frequent injections become necessary with only small amounts of active agent in each injection. Furthermore, the bulk of the carrier substance limits the amount of active agent that may be used in each injection. A further practical drawback to this form of introducing medication follows from the fact that injections are active for only a few days or a week.

Heretofore, containers of many types have been designed for use within the body cavities whereby medicinal preparations are allowed to escape therefrom. Experience has demonstrated however that such previous attempts have not been fully satisfactory for a variety of reasons including the failure of such containers to adequately control the release of the medicament contained therein. Moreover, elaborate arrangements for depositing medication within the body involving the use of dense tablet forms which have a smooth compacted surface, a portion of which is covered with a protective undissolvable coating have also proved in certain cases to be ineffective. That is, the resorption of the medication from the exposed surface thereof cannot be controlled or predicted during the dissolution of such a tablet.

The problem of controlling the release of a medicament over a prolonged period of time when in contact with a living system has also been approached from a chemical point of view. That is to say, that soluble linear polymers have been utilized as drug carriers wherein the drugs are bound to said polymers by ionic and/or coordination bonds. It is further noted that polymeric salts of basic medicaments have also been employed to prolong the release thereof.

A still further approach to the subject problem has been the implantation of polymeric carriers such as three dimensional hydrophilic polymers which are fully insoluble in body liquids. It has been found that biologically active substances can be absorbed into such polymeric hydrophilic carriers and/or freely deposited any place therein, e.g., in its center, either as solids, dispersions, or as solutions. When exposed to living tissue the active substance diffuses gradually into the surrounding body tissue. The amount of active substance penetrating into the organism in a given time unit can be determined in advance according to the known, measured diffusion rate, the thickness of the polymer layer, the size of the contact surface and the concentration difference. In this connection it is noted that the release of the drug cannot be controlled through a single outlet therefor, but rather diffuses through the entire surface of the surrounding polymeric material.

SUMMARY OF THE INVENTION

Therefore, it is an object of the subject invention to provide a device suitable for implanting into living tissue which device controls the prolonged release of a medicament into said living tissue.

Another object of the instant invention is to provide a process by which the rate of diffusion of a biologically active substance can be controlled when said substance is implanted into living tissue.

A further object of the instant invention is to provide an inert structure into which one may insert a biologically active substance and through which said substance can diffuse in a controlled manner.

A still further object of the instant invention is to provide a process for controlling the release of a biologically active substance from within an implantable carrier whereby said biologically active substance diffuses only after reaction with materials present in the surrounding body tissue.

As noted, one aspect of the subject invention resides in an apparatus which is implantable within living tissue. Such an apparatus hereinafter referred to as a difussion cell is constructed in such a way that the diffusion rate of a biologically active material contained therein is directly proportional to the area for diffusion and inversely proportional to the length thereof. The subject structure comprises a capillary having a relatively small bore and corresponding relatively small outside diameter. One end of said diffusion cell is sealed by anyone of several well known techniques. The opposite end is then filled with a biologically active substance and capped with a layer of neutral hydrophilic polymeric material.

The process of the subject invention is directed to the method whereby said biologically active material diffuses from within the diffusion cell into the surrounding body tissue. One may use in connection with the subject invention many relatively non-diffusible biologically active substances which are made diffusible by contact with surrounding body chemicals. That is to say that the biologically active substance employed in connection with said diffusion cell is employed in its non-active form and is later made active and/or diffusible by contact with chemicals contained in the tissue surrounding the implanted diffusion cell.

DETAILED DESCRIPTION OF THE INVENTION

Figure 1:
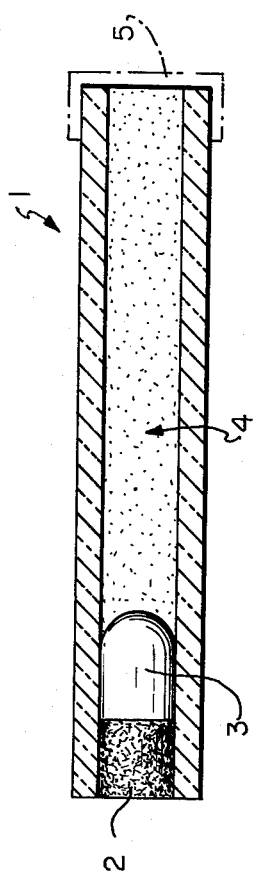
FIG. 1 is a cross-sectional view of the diffusion cell of the subject invention.

As previously noted, the subject invention is directed to an implantable apparatus and process for using same. Said apparatus is illustrated in FIG. 1 of the drawings, wherein 1 comprises the implantable capillary of the subject invention having a relatively small inside and comparable outside diameter. More specifically, said implantable diffusion cell has one end 2 thereof sealed with an impervious material and/or the material of which the capillary itself is made. Embedded therein 3, is a biologically active material, i.e., a drug and/or medicament. Element 4 represents the neutral hydrophilic polymeric material through which the biologically active medicament must diffuse and is an optional layer of polymeric material such as cellulose employed to limit access into the cell of certain body constituents.

According to the subject invention, one may employ a capillary tube 1, fabricated from any inert, impermeable, material such as, for example, glass, inert plastic, and the like. The structure of said capillary diffusion cell should have an inside diameter ranging from about 0.10 mm to about 2.5 mm and a corresponding outside diameter of from about 0.75 mm to about 3 mm although larger tubes may be useful for certain applications. The method of sealing the closed end of the diffusion cell may include plugging same with a totally inert impermeable material and/or sealing the end of the capillary with the same material from which the capillary has been prepared. Exemplary of such impermeable totally inert materials would be wax, various polymers, and the like. In connection with the neutral hydrophilic polymeric portion or layer, it is noted that the rate of diffusion of the medicament and/or biologically active substance contained within the diffusion cell is determined by the amount of the portion or length of said layer. Therefore, the length of said layer can be determined by previously calculating the rate at which said biologically active substance diffuses through the neutral hydrophilic polymer and further the rate by which the necessary body chemicals diffuse through said layer. In general, we have employed polymeric lengths of from about 2 mm to about 14 mm but other lengths of diffusion path, e.g., from about 0.5 to about 30 mm may be used.

As the biologically active material, one may employ any known drug which, because of its chemical nature does not normally diffuse through a neutral hydrophilic polymer, and further which is made diffusible by contact with materials contained in living body tissue which are diffusible through such neutral hydrophilic polymeric materials. This is to say, the process of the subject invention is operative when a non-diffusible biologically active substance is first contacted by normally present body chemicals and made diffusible as a result of such contact. Subsequent thereto, the diffusible biologically active substance passes through the neutral hydrophilic polymeric layer into the surrounding tissue.

However, in its broadest sense the device of this invention could employ biologically active materials of various diffusibilities and solubilities including but not limited to hormones, vitamins, antibiotics, anticoagulants, cancericidal agents, spermicidal agents, vasoactive agents, and other biologically active medicinals and medications effective in the treatment of undesirable conditions existing in or on an animal body or the fluid contained therein. In this connection, the invention may be utilized with such preparations as antibacterials, i.e., sulfathiozole; antibiotics, i.e. penicillin; antifungal agents, i.e., Nystatin; antimalarials, i.e., atabrine; and the antiprotozoans, i.e., hydroxystilbamide isothionate. Antineoplastic agents such as methotrexate; cardiovascular agents, which include digitalis, quinidine and nitroglycerine; contraceptives, for instance spermicidal agents such a hexylresorcinol, may also be utilized in accordance with the present invention. Hormones and the synthetic substitutes and antagonists as represented by the thyroid hormones and by insulin may be used. Immunological agents including for example, tetanus toxoid, renal acting agents, for example, acetazolamide; skeletal muscle relaxants and their antagonists, for example, mephenesin, central nervous system stimulants, for example, ephedrine; and central nervous system depressants, which include the barbiturates in all their various chemical modifications are also included in the invention. Anesthetics which may be used in the novel drug carrier, include procaine, an antihistamine, i.e., benadryl; a detoxicant, dimercaprol; an enzyme, i.e., hyaluronidase. A radioactive isotope which may be included in the novel carrier is iodine 131-tagged albumen.

Examples of additional drugs which may be included in the present drug carriers in accordance with this invention include adrenal corticotrophic hormone; adrenal cortical hormones, such as aldosterone, desoxy corticosterone, hydrocortisone and cortisone; parathormone, pituitrin, estrodiol, progesterone and testosterone.

The actual size and geometry of the cell may be varied depending upon the diffusiblity and solubility of the biologically active substance as well as the total dose necessary for a given application. For example with highly soluble materials or for a large dose it may be desirable to include a bulbous reservoir at the drug end of the capillary.

Materials suitable for use as the neutral hydrophilic polymeric layer are biologically and medicament compatible, non-allergenic, insoluble in and non-irritating to body fluids and or tissues with which the subject device comes in contact. Exemplary materials include but are not limited to agarose, polyacrylamide; and the like.

According to one of the preferred embodiments of the subject invention, the biologically active substance employed in connection herewith is methotrexate in its acid form which as previously indicated is only slightly soluble and therefore relatively non-diffusible through a neutral polymeric hydrogel. The release thereof through said hydrogel, is dominated by the influence of basic ions contained in normal body tissue which subsequent to diffusion through said hydrogel, into the diffusion cell react with the drug thus enabling said drug to diffuse into the surrounding body tissue. Interstitial fluid which will surround the implanted diffusion cell contains numerous diffusible ions. It is noted that a large number of basic ions exist in the interstitial fluid but numerous other chemicals contained therein may also be employed in the unique process of the subject invention whereby the diffusion of same through the neutal hydrophilic layer to make the biologically active substance contained therein diffusible is controlled by controlling the length of the neutral hydrophilic polymeric substance and further the chemical state of the biologically active substance. In this connection, it is also noted that bicarbonate ions are a major constituent of said interstitial fluid with the normal value of same in human plasma being approximately 27 millequiv/l. Once the cell is implanted, either surgically and/or by means of a large gauge hypodermic, the plasma concentration of the active medicament can be determined. As a result, it was determined that the subject cell provided for a prolonged release of the biologically active substance over an extended period of time.

The subject invention will now be further illustrated by the following more detailed examples thereof. Said examples are not deemed as being limited thereof, but rather, serve only to further amplify the subject inven-

EXAMPLE I

Sections of a glass capillary tube were lightly flame polished and filled by capillary action with a solution of 1 percent agarose prepared with 0.9 percent sodium chloride. A thick slurry of methotrexate was then forced into one end thereof and that end was then sealed by pressing same through a shallow layer of wet soft utility type wax. The diffusion cell was then treated with a room temperature vulcanizing silicone rubber to eliminate any problem with motion of the wax plug.

EXAMPLE II

The diffusion cells, prepared in Example I, were placed in a solution of 0.25 percent sodium bicarbonate and 0.9 percent sodium chloride, to simulate in vivo conditions and approach a steady state release rate. It was determined that for a gel length of one centimeter at a room temperature of 20–23 C, the process took approximately 3 weeks. The long transition results from the requirement that sufficient biocarbonate must diffuse through the hydrogel into the drug to infiltrate part of it and establish a gradient of methotrexate ion.

EXAMPLE III

Diffusion cells prepared according to or substantially according to Example I, having a predicted release rate of from 0.2 to 9 µg/hr in vivo as determined by in vitro testing were implanted in ether anesthetized mice (24g) for a variety of toxicologic and biochemical studies. The smaller cells were inserted by means of a 13 gauge trocar filled with normal saline and the larger cells were pushed through a small stab wound at the same site. Plasma concentration after implantation was determined using 0.8 µg/hr cells. The plasma concentration was found to reach 90 percent of plateau within 6 hours.

EXAMPLE IV

Several of the diffusion cells were removed from the mice by locating the same manually and pushing said cells through a tiny incision in the skin. The removed cells were then checked in vitro and found to sustain a rate of release in the absence of visible drug depletion following up to 13 days implantation.

While the subject invention has been specifically illustrated in connection with methotrexate, it is noted that same is not limited thereto. That is to say, that the subject diffusion cell may be appropriately prepared having various neutral hydrophilic polymeric gel layers of any suitable length so as to control the desired release of any biologically active material. Moreover, any drug which is relatively insoluble may be incorporated therein and made soluble and or diffusible by contact with diffusing body chemicals.

The embodiments of the invention in which an exclusive property or privilege is claimed are defined as follows:

1. A diffusion cell comprising a hollow small diameter capillary tube containing therein a biologically active substance adjacent one end, said one end thereof being sealed with an inert impervious material and the rest of the tube and the other end thereof closed with a neutral hydrophilic polymeric material.

2. The apparatus of claim 1, wherein said neutral hydrophilic polymeric material is agarose.

3. The apparatus of claim 1, wherein said neutral hydrophilic polymeric material has a length of from about 2 to 14 mm.

4. A process for controlling the release of a biologically active substance in contact with living tissue which comprises implanting a diffusion cell comprising a small capillary tube containing a non-diffusible biologically active substance therein adjacent one end, which capillary tube has said one end thereof sealed with an impervious insoluble material and the rest of the tube and the other end thereof filled with a neutral hydrophilic polymeric gel.

5. The process of claim 4, wherein said neutral hydrophilic polymeric gel is agarose.

6. The process of claim 4, wherein said biologically active substance is methotrexate.

7. The process of claim 4, wherein said neutral hydrophilic polymeric material contained in said diffusion cell has a length of from about 2 to about 14 mm.

* * * * *

UNITED STATES PATENT AND TRADEMARK OFFICE
CERTIFICATE OF CORRECTION

PATENT NO. : 3,946,734
DATED : March 30, 1976
INVENTOR(S) : Robert L. Dedrick, et al It is certified that error appears in the above-identified patent and that said Letters Patent are hereby corrected as shown below:

On the cover sheet correct the assignee to read:

[73] Assignee:
The United States of America as represented by the Secretary of Health, Education, and Welfare, Washington, D.C.

Signed and Sealed this

Twentieth Day of July 1976

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

PATENT NO. : 3,946,734
DATED : March 30, 1976
INVENTOR(S) : Robert L. Dedrick, et al It is certified that error appears in the above–identified patent and that said Letters Patent are hereby corrected as shown below:

On the cover sheet item [73] should read as shown.

--The Government of The United States--.

This certificate supersedes Certificate of Correction issued July 20, 1976.

Signed and Sealed this

Seventeenth Day of August 1976

[SEAL]

Attest:

RUTH C. MASON
Attesting Officer

C. MARSHALL DANN
Commissioner of Patents and Trademarks